US012174109B2

(12) United States Patent
Ma et al.

(10) Patent No.: US 12,174,109 B2
(45) Date of Patent: *Dec. 24, 2024

(54) OPTICAL CALIBRATION TOOL

(71) Applicant: DELTA ELECTRONICS, INC., Taoyuan (TW)

(72) Inventors: Bo Ma, Taoyuan (TW); Jei-Yin Yiu, Taoyuan (TW); Yu-Kai Kao, Taoyuan (TW); I-An Yen, Taoyuan (TW); Chun-Jung Li, Taoyuan (TW); Shu-Ting Hsu, Taoyuan (TW); Song-Bin Huang, Taoyuan (TW); Ni-Chin Ko, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,027

(22) Filed: Oct. 6, 2023

(65) Prior Publication Data

US 2024/0035955 A1 Feb. 1, 2024

Related U.S. Application Data

(63) Continuation of application No. 17/013,840, filed on Sep. 7, 2020, now Pat. No. 11,815,445.

(30) Foreign Application Priority Data

Jan. 31, 2020 (TW) .................................. 109102937

(51) Int. Cl.
*G01N 21/01* (2006.01)
*B01L 7/00* (2006.01)
(Continued)

(52) U.S. Cl.
CPC .............. *G01N 21/01* (2013.01); *B01L 7/525* (2013.01); *B01L 2200/148* (2013.01);
(Continued)

(58) Field of Classification Search
CPC ... G01N 21/01; B01L 7/525; B01L 2200/148; B01L 2300/0663; G02B 5/205; G02B 7/1821; G02B 26/0825; G02B 27/144
(Continued)

(56) References Cited

U.S. PATENT DOCUMENTS

| 3,645,627 A | 2/1972 | Brody et al. |
| 6,067,156 A | 5/2000 | Slater et al. |

(Continued)

FOREIGN PATENT DOCUMENTS

| CN | 110018139 A | 7/2019 |
| JP | S63315938 A | 12/1988 |

(Continued)

*Primary Examiner* — Wyatt A Stoffa
*Assistant Examiner* — Mitchell T Oestreich
(74) *Attorney, Agent, or Firm* — CKC & Partners Co., LLC (57) ABSTRACT

An optical calibration tool includes a first body, a light emitter, a light receiver, a second body, and a light reflecting member. The first body has a first engaging port and a second engaging port. The light emitter and the light receiver are disposed in the first body. The second body has a third engaging port and a channel communicated with each other. The third engaging port is configured to selectively engage one of the first engaging port and the second engaging port. When the third engaging port is engaged with the first engaging port, the light emitter is optically coupled to the light reflecting member. When the third engaging port is engaged with the second engaging port, the light receiver is optically coupled to the light reflecting member.

10 Claims, 10 Drawing Sheets

(51) Int. Cl.
  *G02B 5/20* (2006.01)
  *G02B 7/182* (2021.01)
  *G02B 26/08* (2006.01)
  *G02B 27/14* (2006.01)

(52) U.S. Cl.
  CPC ....... *B01L 2300/0663* (2013.01); *G02B 5/205* (2013.01); *G02B 7/1821* (2013.01); *G02B 26/0825* (2013.01); *G02B 27/144* (2013.01)

(58) Field of Classification Search
  USPC .................................................... 435/286.2
  See application file for complete search history.

(56) References Cited

U.S. PATENT DOCUMENTS

| | | | |
|---|---|---|---|
| 6,078,388 A | 6/2000 | Njamfa | |
| 6,246,525 B1 | 6/2001 | Ikami | |
| 6,498,690 B2 | 12/2002 | Ramm et al. | |
| 6,746,864 B1 | 6/2004 | McNeil et al. | |
| 6,852,986 B1 | 2/2005 | Lee et al. | |
| 6,982,166 B2 | 1/2006 | Sandell | |
| 7,015,484 B2 | 3/2006 | Gillispie et al. | |
| 7,148,043 B2 | 12/2006 | Kordunsky et al. | |
| 7,273,749 B1 | 9/2007 | Wittwer et al. | |
| 7,289,217 B2 | 10/2007 | Boege et al. | |
| 7,315,376 B2 | 1/2008 | Bickmore, Jr. et al. | |
| 7,369,227 B2 | 5/2008 | Gutekunst et al. | |
| 7,663,750 B2 | 2/2010 | Bahatt et al. | |
| 7,687,260 B2 | 3/2010 | Gutekunst | |
| 7,700,928 B2 | 4/2010 | Rasnow et al. | |
| 8,278,114 B2 | 10/2012 | Gambini et al. | |
| 8,557,569 B2 | 10/2013 | Boege et al. | |
| 8,865,473 B2 | 10/2014 | Gambini et al. | |
| 8,900,828 B2 | 12/2014 | Smith et al. | |
| 8,921,098 B2 | 12/2014 | Gambini et al. | |
| 8,987,685 B2 | 3/2015 | Fawcett et al. | |
| 9,080,207 B2 | 7/2015 | Handique et al. | |
| 9,096,892 B1 | 8/2015 | Klemer et al. | |
| 10,006,862 B2 | 6/2018 | Lair et al. | |
| 10,036,058 B2 | 7/2018 | Baumgartner et al. | |
| 2001/0046050 A1 | 11/2001 | Hoyt | |
| 2003/0011772 A1 | 1/2003 | Abe et al. | |
| 2003/0117623 A1 | 6/2003 | Tokhtuev et al. | |
| 2004/0178357 A1 | 9/2004 | King | |
| 2005/0128476 A1 | 6/2005 | Zhao | |
| 2005/0133724 A1 | 6/2005 | Hsieh et al. | |
| 2006/0289786 A1 | 12/2006 | Taylor et al. | |
| 2007/0114444 A1* | 5/2007 | Reid .................. | G01N 21/6452 250/227.28 |
| 2008/0116382 A1 | 5/2008 | Eckert et al. | |
| 2008/0277595 A1 | 11/2008 | Lundquist et al. | |
| 2009/0009767 A1 | 1/2009 | Boege et al. | |
| 2014/0273181 A1 | 9/2014 | Abbott et al. | |
| 2014/0283945 A1 | 9/2014 | Jones et al. | |
| 2015/0232916 A1 | 8/2015 | Rasmussen et al. | |

FOREIGN PATENT DOCUMENTS

| | | |
|---|---|---|
| JP | 2005-331319 A | 12/2005 |
| JP | 55-25380 B2 | 6/2014 |
| TW | I636248 B | 9/2018 |
| TW | I654309 B | 3/2019 |

\* cited by examiner

OPTICAL CALIBRATION TOOL

CROSS-REFERENCE TO RELATED APPLICATION

This application is a Continuation Application of U.S. application Ser. No. 17/013,840, filed on Sep. 7, 2020, which claims priority of Taiwan Application Serial Number 109102937, filed on Jan. 31, 2020, the entirety of which is incorporated by reference herein.

BACKGROUND

Technical Field

The present disclosure relates to an optical calibration tool.

Description of Related Art

One conventional approach of calibrating a real-time quantitative polymerase chain reaction (qPCR) instrument is using fluorescence calibration kit samples. However, there are many disadvantages due to its inherent properties. Typically, the fluorescent calibration kit samples have to be stored under room temperature, and the life of shelf is very short once the kit is unsealed. Typically, the shelf life suppliers suggested are usually 6 months. Also, repeated thawing process between room temperature and freezing temperature cause the degradation of fluorescent calibration kit.

Accordingly, how to provide an optical calibration tool to solve the aforementioned problems becomes an important issue to be solved by those in the industry.

SUMMARY

An aspect of the disclosure is to provide an optical calibration tool which can effectively solve the aforementioned problems.

According to an embodiment of the disclosure, an optical calibration tool includes a first body, a light emitter, a light receiver, a second body, and a light reflecting member. The first body has a first engaging port and a second engaging port. The light emitter and the light receiver are disposed in the first body. The second body has a third engaging port and a channel communicated with each other. The third engaging port is configured to selectively engage one of the first engaging port and the second engaging port. When the third engaging port is engaged with the first engaging port, the light emitter is optically coupled to the light reflecting member. When the third engaging port is engaged with the second engaging port, the light receiver is optically coupled to the light reflecting member.

In an embodiment of the disclosure, the second body has a light transmitting portion adjoining the channel. When the third engaging port is engaged with the first engaging port, the light emitter is optically coupled to the light transmitting portion via the light reflecting member. When the third engaging port is engaged with the second engaging port, the light receiver is optically coupled to the light transmitting portion via the light reflecting member.

In an embodiment of the disclosure, the light transmitting portion is a hole.

In an embodiment of the disclosure, the second body has two light transmitting portions. Said two light transmitting portions are respectively located at opposite sides of the second body. The light reflecting member is located between said two light transmitting portions.

In an embodiment of the disclosure, the optical calibration tool further includes an actuating member. The actuating member is configured to rotate the light reflecting member.

In an embodiment of the disclosure, the optical calibration tool further includes an actuating member. The actuating member is configured to deform the light reflecting member.

In an embodiment of the disclosure, the light reflecting member includes a prism and a light splitting layer. The prism has two surfaces connected to each other and arranged between said two light transmitting portions. The light splitting layer covers said two surfaces.

In an embodiment of the disclosure, the optical calibration tool further includes a neutral density filter. The neutral density filter is disposed in the first body and adjoins the second engaging port.

In an embodiment of the disclosure, the optical calibration tool further includes a lens group. The lens group is disposed in the channel and adjoins the third engaging port.

According to an embodiment of the disclosure, an optical calibration tool is applied to a real-time quantitative polymerase chain reaction (qPCR) instrument. The qPCR instrument includes an inspection slot. The inspection slot has a light incident region and a light exit region. The optical calibration tool includes a first body, a light emitter, a light receiver, a second body, and a light reflecting member. The first body has a first engaging port and a second engaging port. The light emitter is disposed in the first body. The light receiver is disposed in the first body. The second body has a third engaging port and a channel communicated with each other. The third engaging port is configured to selectively engage one of the first engaging port and the second engaging port. The light reflecting member is disposed in the channel and configured to be selectively optically coupled to one of the light incident region and the light exit region as the second body rotates relative to the inspection slot.

Accordingly, in the optical calibration tool of the present disclosure, by engaging the third engaging port of the second body to the first engaging port of the first body, the light emitter in the optical calibration tool can be used to calibrate the light receiver in the qPCR instrument. Relatively, by engaging the third engaging port of the second body to the second engaging port of the first body, the light receiver in the optical calibration tool can be used to calibrate the light emitter in the qPCR instrument. That is, the optical calibration tool of the present disclosure can form different functional modules by different combinations of the first body and the second body. Furthermore, a user only needs to insert the second body into the inspection slot of the qPCR instrument to optically couple the light emitter of the optical calibration tool to the light receiver in the qPCR instrument, or to optically couple the light receiver of the optical calibration tool to the light emitter in the qPCR instrument. As such, the optical calibration tool of the present disclosure is easy for the user to operate, so that the calibration procedure can be performed quickly.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts. However, specific structural and functional details disclosed herein are merely representative for purposes of describing example embodiments, and thus may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope of the disclosure.

Figure 1:
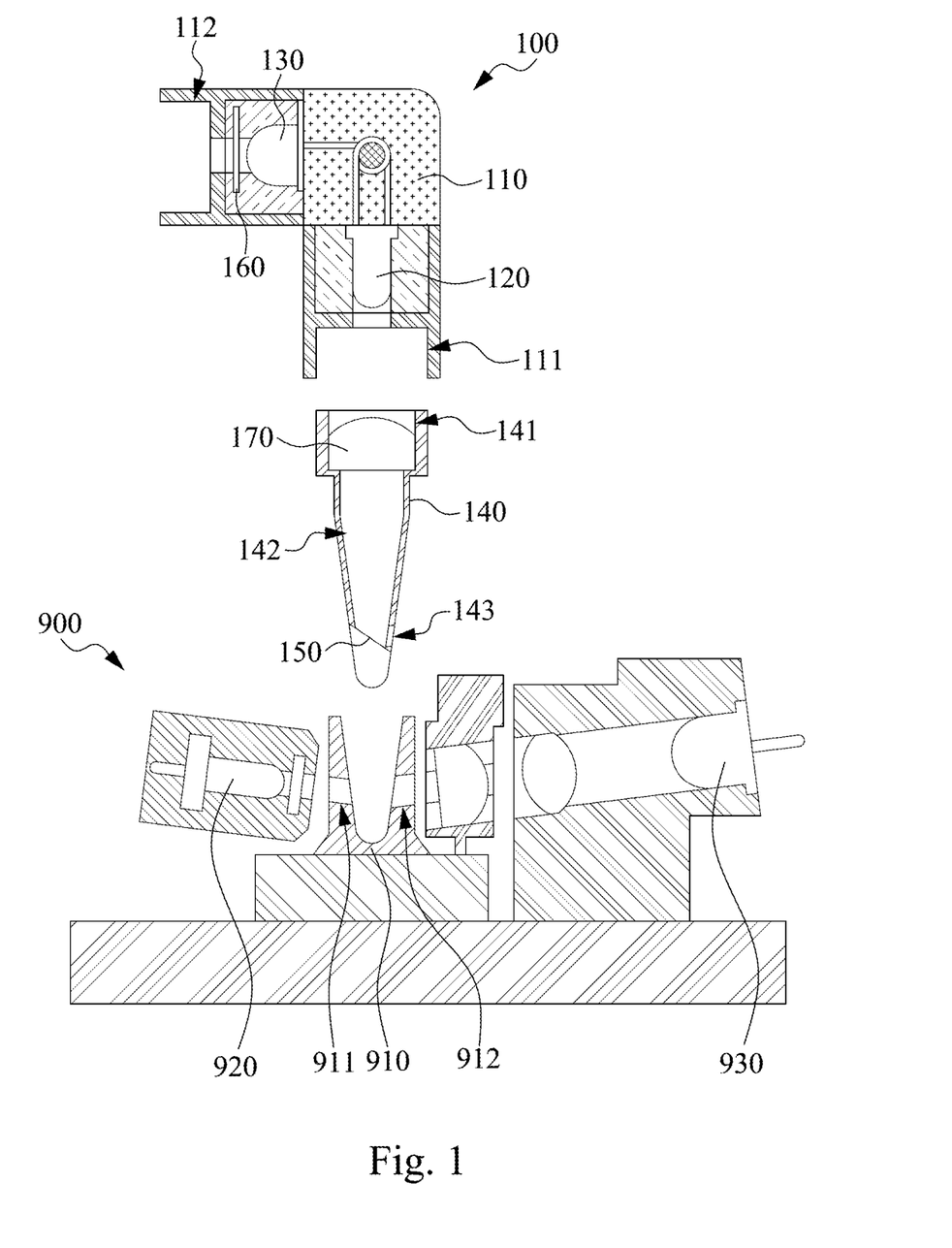
FIG. 1 is a cross-sectional view of an optical calibration tool and a real-time quantitative polymerase chain reaction (qPCR) instrument before assembly according to an embodiment of the present disclosure.
Figure 2A:
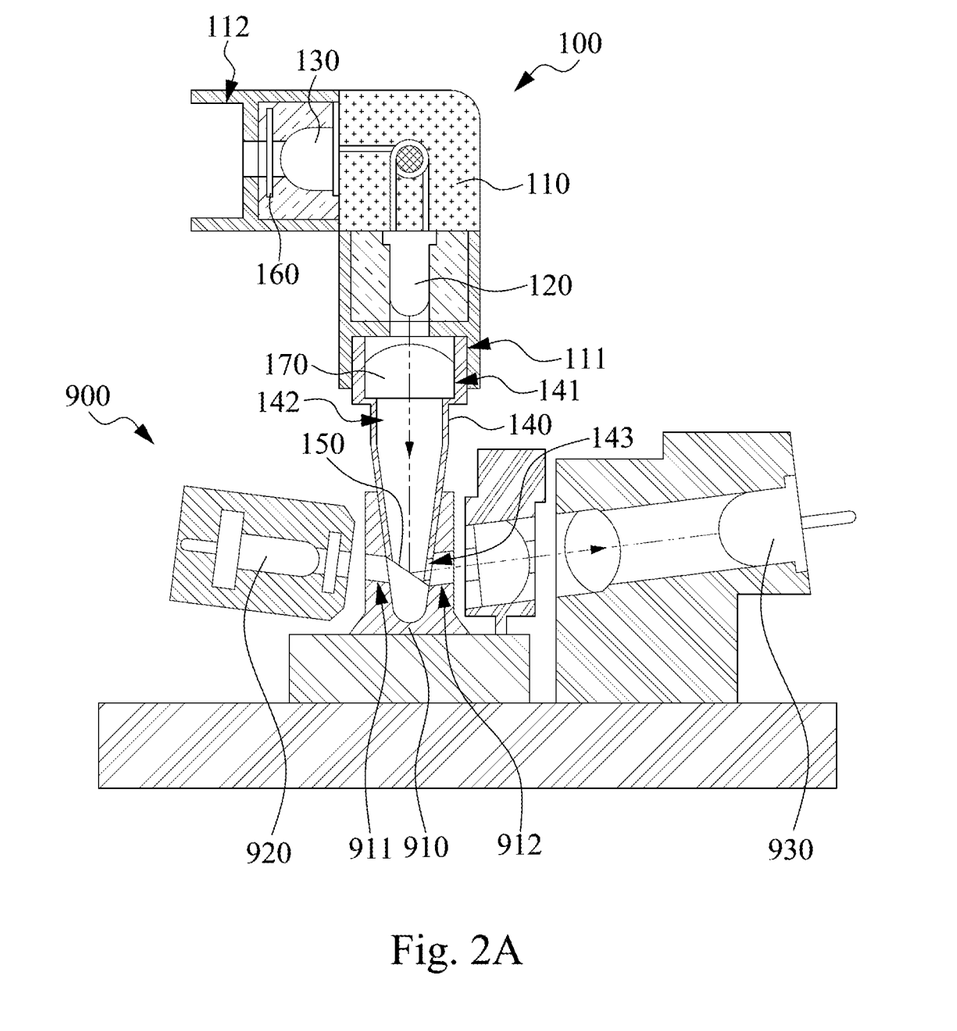
FIG. 2A is a cross-sectional view of the optical calibration tool and the qPCR instrument in FIG. 1 after assembly.
Figure 2B:
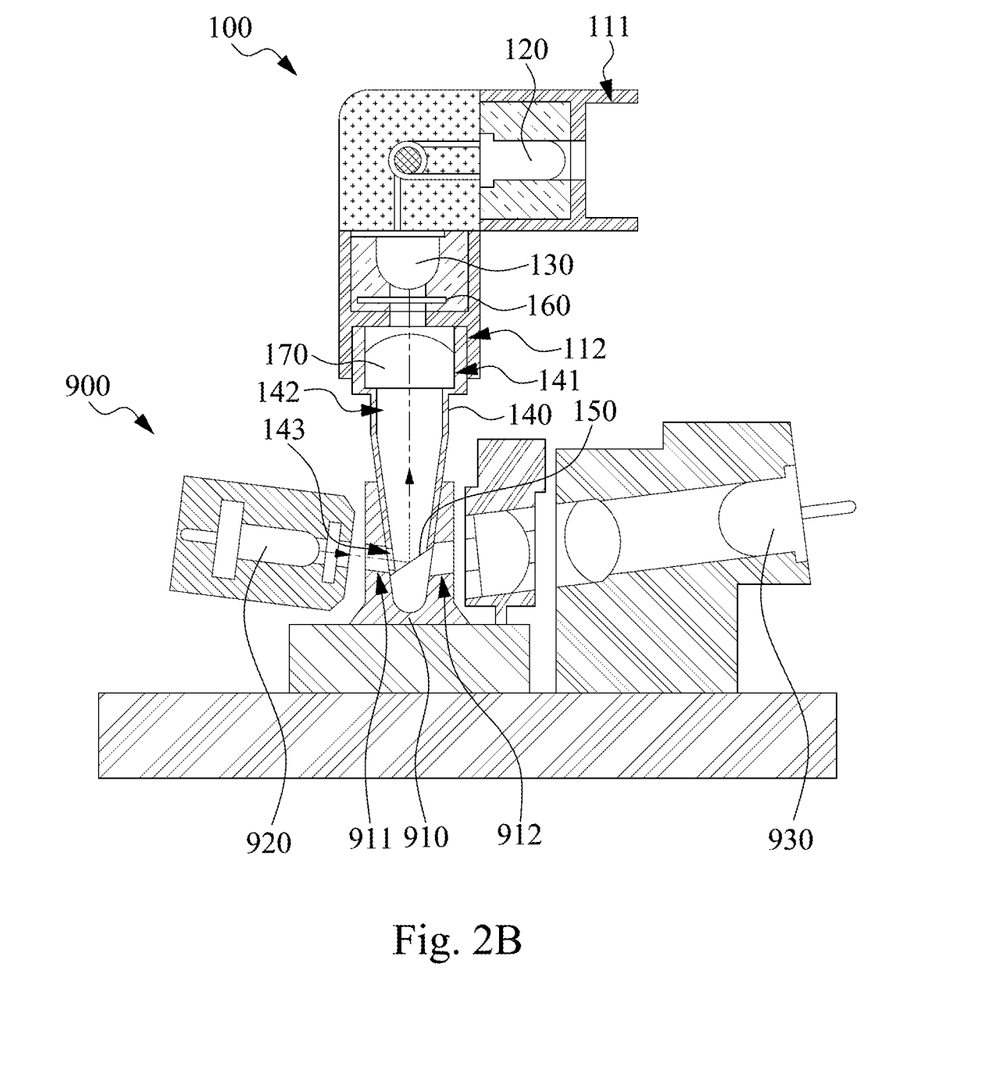
FIG. 2B is another cross-sectional view of the optical calibration tool and the qPCR instrument in FIG. 2A.

Reference is made to FIGS. 1 to 2B. FIG. 1 is a cross-sectional view of an optical calibration tool 100 and a real-time quantitative polymerase chain reaction (qPCR) instrument 900 before assembly according to an embodiment of the present disclosure. FIG. 2A is a cross-sectional view of the optical calibration tool 100 and the qPCR instrument 900 in FIG. 1 after assembly. FIG. 2B is another cross-sectional view of the optical calibration tool 100 and the qPCR instrument 900 in FIG. 2A. As shown in FIGS. 1 to 2B, in the present embodiment, the optical calibration tool 100 is applied to the qPCR instrument 900. The qPCR instrument 900 includes an inspection slot 910, a light emitter 920, and a light receiver 930. The inspection slot 910 has a light incident region 911 and a light exit region 912. When the qPCR instrument 900 is working, an inspector may place a sample (for example, accommodated in a transparent container) in the inspection slot 910, emit light through the light incident region 911 of the inspection slot 910 to the sample by the light emitter 920, and receives the light passing through the sample through the light exit region 912 of the inspection slot 910 by the light receiver 930. Hence, the inspector can obtain the physical, chemical, or biological characteristics or parameters of the sample according to the light receiving signal of the light receiver 930. The optical calibration tool 100 is used to inspect whether the light emitter 920 and the light receiver 930 of the qPCR instrument 900 are abnormal.

The optical calibration tool 100 includes a first body 110, a light emitter 120, a light receiver 130, a second body 140, and a light reflecting member 150. The first body 110 has a first engaging port 111 and a second engaging port 112. The light emitter 120 and the light receiver 130 are disposed in the first body 110. The second body 140 has a third engaging port 141 and a channel 142 communicated with each other. The third engaging port 141 is configured to engage the first engaging port 111 (as shown in FIG. 2A) or the second engaging port 112 (as shown in FIG. 2B). The light reflecting member 150 is disposed in the channel 142 and configured to be selectively optically coupled to one of the light incident region 911 and the light exit region 912 of the inspection slot 910 as the second body 140 rotates relative to the inspection slot 910.

In some embodiments, when the third engaging port 141 is engaged with the first engaging port 111, the first engaging port 111 is sleeved on the outer edge of the third engaging port 141, as shown in FIG. 2A, but the present disclosure is not limited in this regard. In some embodiments, when the third engaging port 141 is engaged with the second engaging port 112, the second engaging port 112 is sleeved on the outer edge of the third engaging port 141, as shown in FIG. 2B, but the present disclosure is not limited in this regard.

Specifically, as shown in FIG. 2A, when the third engaging port 141 is engaged with the first engaging port 111, the light emitter 120 of the optical calibration tool 100 is optically coupled to the light reflecting member 150. In other words, the light emitted by the light emitter 120 of the optical calibration tool 100 can be reflected by the light reflecting member 150 to the light receiver 930 of the qPCR instrument 900. Hence, a user can determine whether the light receiver 930 of the qPCR instrument 900 is abnormal and needs to be calibrated according to the received light signal. As shown in FIG. 2B, when the third engaging port 141 is engaged with the second engaging port 112, the light receiver 130 of the optical calibration tool 100 is optically coupled to the light reflecting member 150. In other words, the light emitted by the light emitter 920 of the qPCR instrument 900 can be reflected by the light reflecting member 150 to the light receiver 130 of the optical calibration tool 100. Hence, the user can determine whether the light emitter 920 of the qPCR instrument 900 is abnormal and needs to be calibrated according to the received light signal.

In some embodiments, the light reflecting member 150 is a reflective coating located in the channel 142 and at the bottom of the second body 140, but the present disclosure is not limited in this regard. In some embodiments, the light reflecting member 150 is a metal layer, but the present disclosure is not limited in this regard.

In some embodiments, the second body 140 has a light transmitting portion 143 adjoining the channel 142. As shown in FIG. 2A, when the third engaging port 141 is engaged with the first engaging port 111 and the light transmitting portion 143 is aligned with the light exit region 912, the light emitter 120 of the optical calibration tool 100 is optically coupled to the light receiver 930 of the qPCR instrument 900 sequentially via the light reflecting member 150 and the light transmitting portion 143. As shown in FIG. 2B, when the third engaging port 141 is engaged with the second engaging port 112 and the light transmitting portion 143 is aligned with the light incident region 911, the light receiver 130 of the optical calibration tool 100 is optically coupled to the light emitter 920 of the qPCR instrument 900 sequentially via the light reflecting member 150 and the light transmitting portion 143.

In some embodiments, the light transmitting portion 143 is a hole but the present disclosure is not limited in this regard. In some other embodiments, the light transmitting portion 143 includes a transparent material, such as glass, optical-grade polymer, ceramic, or the like.

In some embodiments, as shown in FIG. 2B, the optical calibration tool 100 further includes a neutral density filter 160. The neutral density filter 160 is disposed in the first body 110 and adjoins the second engaging port 112. With the arrangement of the neutral density filter 160, the intensity of the light received by the light receiver 130 of the optical calibration tool 100 from the light emitter 920 of the qPCR instrument 900 can be appropriately reduced.

In some embodiments, the material of the second body 140 includes black anodized aluminum to reduce light scattering in the channel 142, but the present disclosure is not limited in this regard.

In some embodiments, as shown in FIGS. 2A and 2B, the optical calibration tool 100 further includes a lens group 170. The lens group 170 is disposed in the channel 142 and adjoins the third engaging port 141. When the light emitter 120 of optical calibration tool 100 is optically coupled to the light receiver 930 of the qPCR instrument 900 (as shown in FIG. 2A), the lens group 170 can converge and focus the light emitted by the light emitter 120 of the optical calibration tool 100 to the light receiver 930 of the qPCR instrument 900. When the light receiver 130 of the optical calibration tool 100 is optically coupled to the light emitter 920 of the qPCR instrument 900 (as shown in FIG. 2B), the lens group 170 can converge and focus the light emitted by the light emitter 920 of the qPCR instrument 900 to the light receiver 130 of the optical calibration tool 100.

In some other embodiments, the material of the lens group 170 includes glass, optical-grade polymer, ceramic, or the like.

In some embodiments, numbers of the inspection slot(s) 910, the light emitter(s) 920, and the light receiver(s) 930 of the qPCR instrument 900 are plural and consistent. In some embodiments, numbers of the light emitter(s) 120 of the optical calibration tool 100 and the light receiver(s) 930 of the qPCR instrument 900 are consistent. In some embodiments, a number of the light emitter(s) 120 of the optical calibration tool 100 is smaller than a number of the light receiver(s) 930 of the qPCR instrument 900. In some embodiments, numbers of the light receiver(s) 130 of the optical calibration tool 100 and the light emitter(s) 920 of the qPCR instrument 900 are consistent.

In some embodiments, the light emitter 120 of the optical calibration tool 100 is a light emitting diode or a laser, but the present disclosure is not limited in this regard.

Figure 3A:
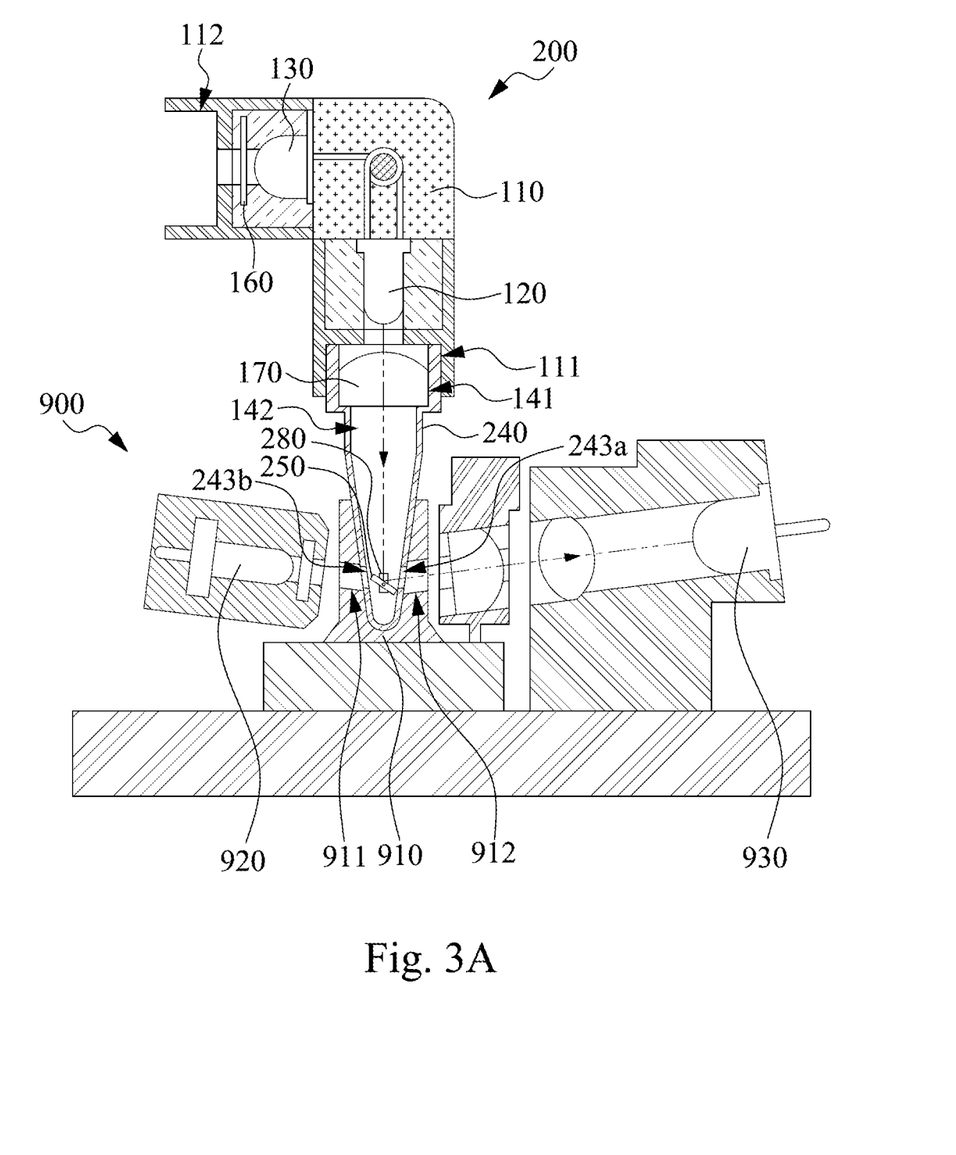
FIG. 3A is a cross-sectional view of an optical calibration tool and the qPCR instrument after assembly according to an embodiment of the present disclosure.
Figure 3B:
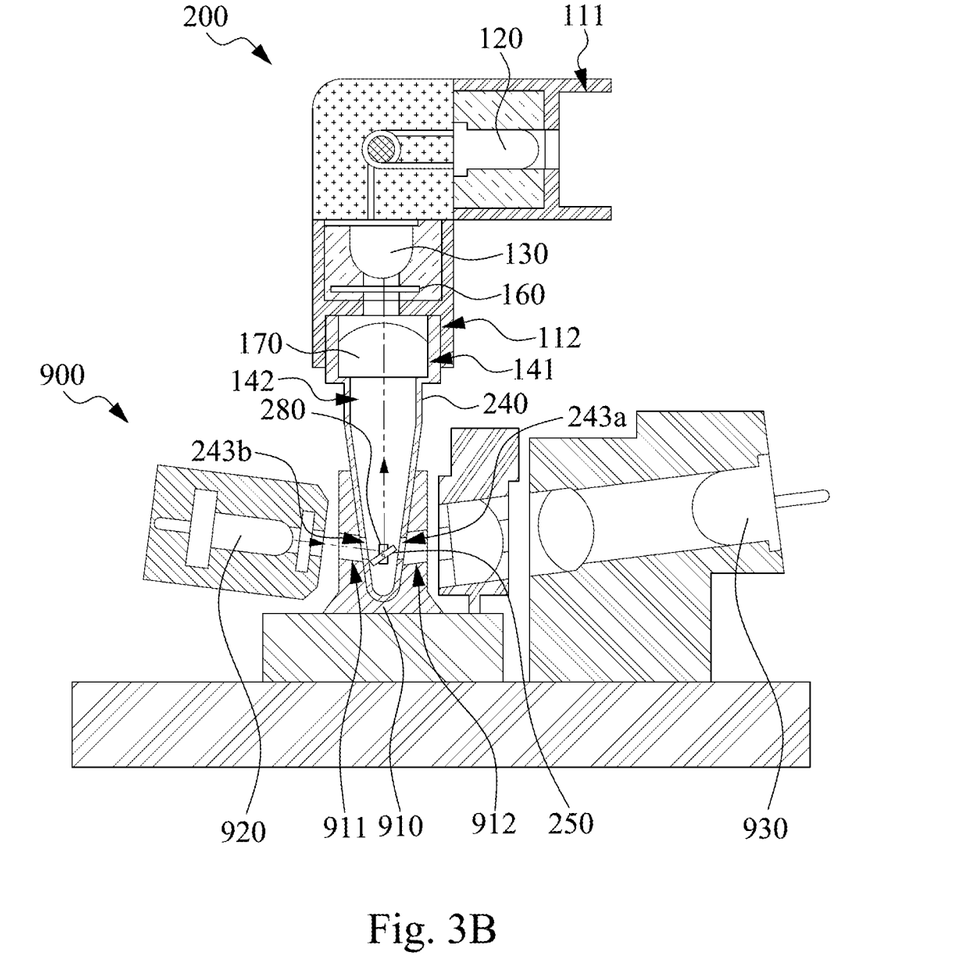
FIG. 3B is another cross-sectional view of the optical calibration tool and the qPCR instrument in FIG. 3A.

Reference is made to FIGS. 3A and 3B. FIG. 3A is a cross-sectional view of an optical calibration tool 200 and the qPCR instrument 900 after assembly according to an embodiment of the present disclosure. FIG. 3B is another cross-sectional view of the optical calibration tool 200 and the qPCR instrument 900 in FIG. 3A. As shown in FIGS. 3A and 3B, one difference between this embodiment and the embodiment shown in FIG. 2A is that the second body 240 of the optical calibration tool 200 of this embodiment has two light transmitting portions 243*a*, 243*b*. The light transmitting portions 243*a*, 243*b* are respectively located at opposite sides of the second body 240. The light reflecting member 250 is located between the light transmitting portions 243*a*, 243*b*.

Another difference between this embodiment and the embodiment shown in FIG. 2A is that the optical calibration tool 200 of this embodiment further includes an actuating member 280. The actuating member 280 is configured to rotate the light reflecting member 250. As shown in FIG. 3A, when the third engaging port 141 is engaged with the first engaging port 111, the light reflecting member 250 can be rotated by the actuating member 280 such that the light emitter 120 of the optical calibration tool 200 is optically coupled to the light receiver 930 of the qPCR instrument 900 sequentially via the light reflecting member 250 and the light transmitting portion 243*a*. As shown in FIG. 3B, when the third engaging port 141 is engaged with the second engaging port 112, the light reflecting member 250 can be rotated by the actuating member 280 such that the light receiver 130 of the optical calibration tool 200 is optically coupled to the light emitter 920 of the qPCR instrument 900 sequentially via the light reflecting member 250 and the light transmitting portion 243*b*. Hence, the user only needs to use the actuating member 280 to rotate the light reflecting member 250 to inspect the light emitter 920 and the light receiver 930 of the qPCR instrument 900 without plugging or rotating the second body 240 relative to the inspection slot 910, so that the calibration process can be performed quickly.

In some embodiments, the light reflecting member 250 is a reflector, but the present disclosure is not limited in this regard.

Figure 4A:
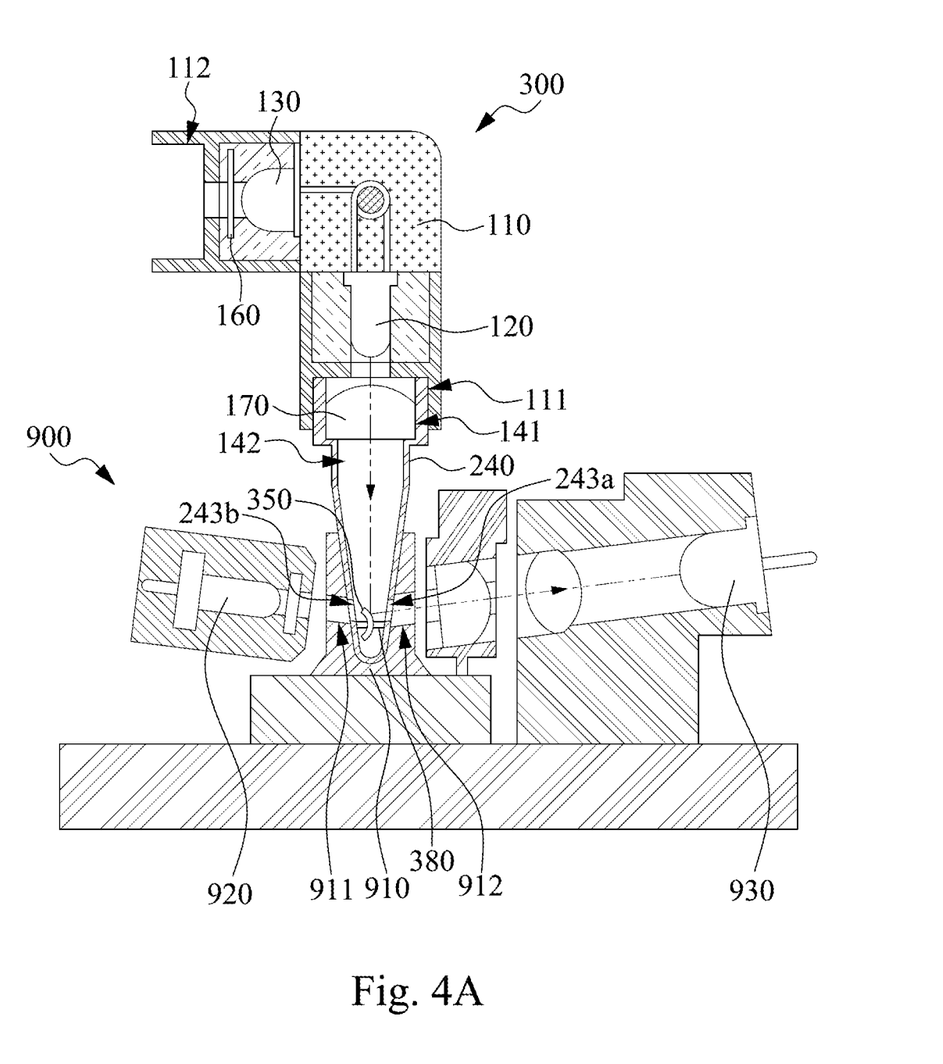
FIG. 4A is a cross-sectional view of an optical calibration tool and the qPCR instrument after assembly according to an embodiment of the present disclosure.
Figure 4B:
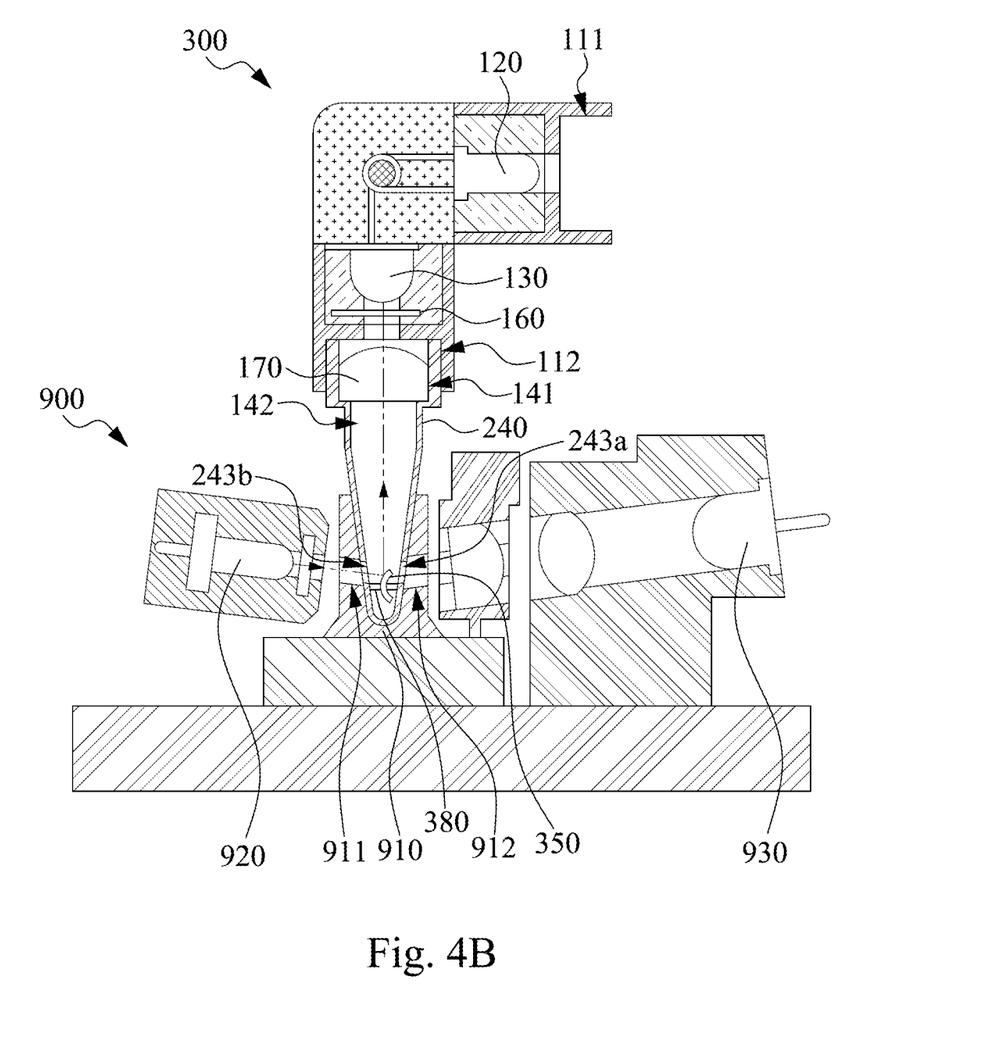
FIG. 4B is another cross-sectional view of the optical calibration tool and the qPCR instrument in FIG. 4A.

Reference is made to FIGS. 4A and 4B. FIG. 4A is a cross-sectional view of an optical calibration tool 300 and the qPCR instrument 900 after assembly according to an embodiment of the present disclosure. FIG. 4B is another cross-sectional view of the optical calibration tool 300 and the qPCR instrument 900 in FIG. 4A. As shown in FIGS. 4A and 4B, one difference between this embodiment and the embodiment shown in FIG. 3A is that the optical calibration tool 300 of this embodiment uses different a light reflecting member 350 and an actuation member 380.

Specifically, the actuating member 380 is configured to deform the light reflecting member 350. As shown in FIG. 4A, when the third engaging port 141 is engaged with the first engaging port 111, the actuating member 380 can be used to apply force to deform and bend the light reflecting member 350 (for example, to apply a force to the center of the light reflecting member 350 to the right), such that the light emitter 120 of the optical calibration tool 300 is optically coupled to the light receiver 930 of the qPCR instrument 900 sequentially via the light reflecting member 350 and the light transmitting portion 243*a*. As shown in FIG. 4B, when the third engaging port 141 is engaged with the second engaging port 112, the actuating member 380 can be used to apply force to deform and bend the light reflecting member 350 (for example, to apply a force to the center of the light reflecting member 350 to the left), such that the light receiver 130 of the optical calibration tool 300 is optically coupled to the light emitter 920 of the qPCR instrument 900 sequentially via the light reflecting member 350 and the light transmitting portion 243*b*. Hence, the user only needs to use the actuating member 380 to deform the light reflecting member 350 to inspect the light emitter 920 and the light receiver 930 of the qPCR instrument 900 without plugging or rotating the second body 240 relative to the inspection slot 910, so that the calibration process can be performed quickly.

In some embodiments, the light reflecting member 350 may be a flexible reflective sheet, but the present disclosure is not limited in this regard.

Figure 5A:
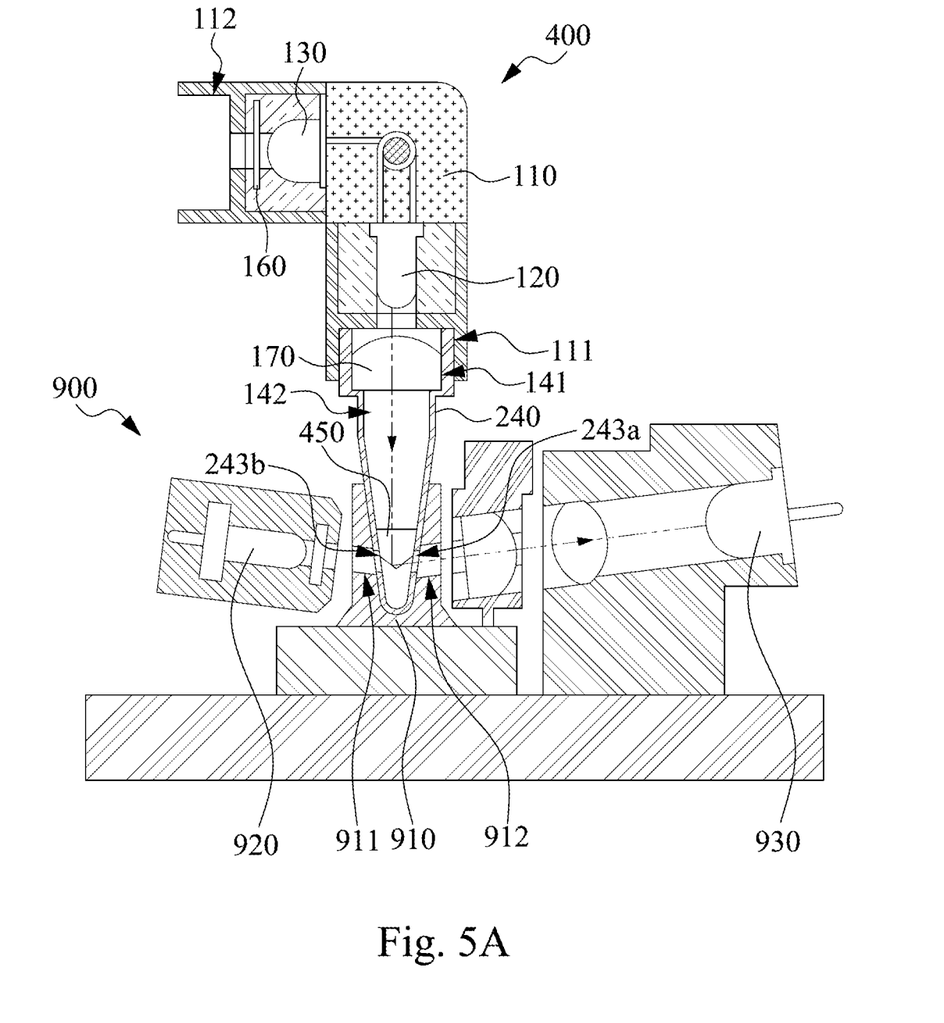
FIG. 5A is a cross-sectional view of an optical calibration tool and the qPCR instrument after assembly according to an embodiment of the present disclosure.
Figure 5B:
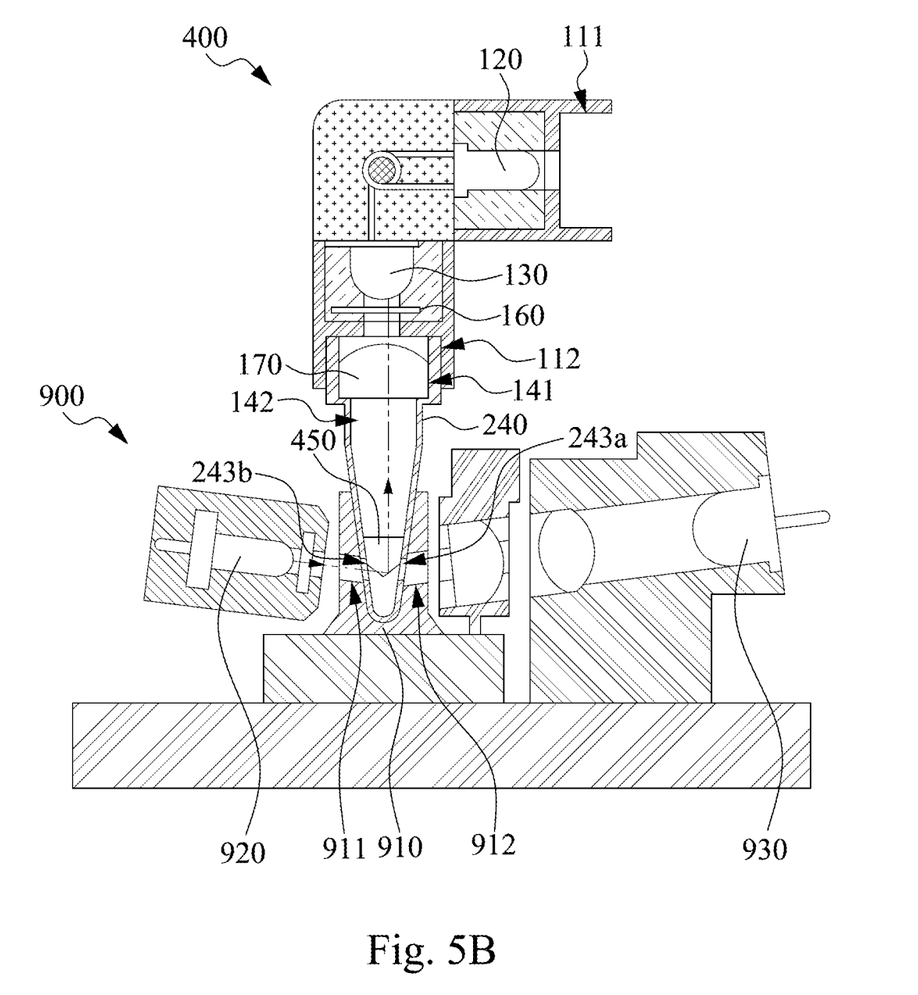
FIG. 5B is another cross-sectional view of the optical calibration tool and the qPCR instrument in FIG. 5A.
Figure 6:
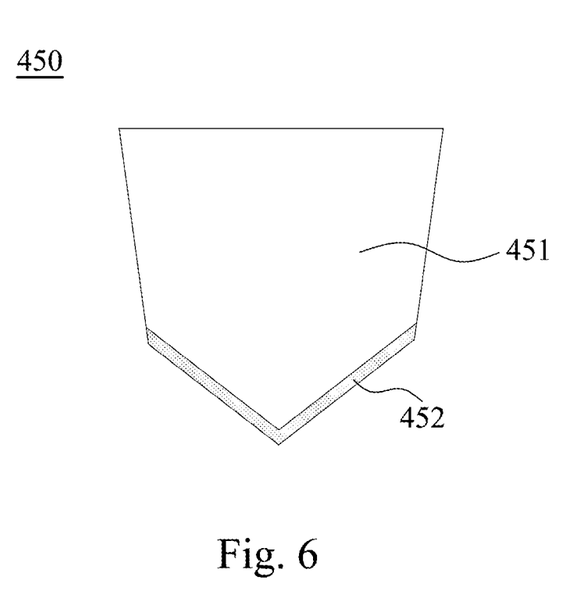
FIG. 6 is a schematic diagram of a light reflecting member in FIG. 5A.

Reference is made to FIGS. 5A to 6. FIG. 5A is a cross-sectional view of an optical calibration tool 400 and the qPCR instrument 900 after assembly according to an embodiment of the present disclosure. FIG. 5B is another cross-sectional view of the optical calibration tool 400 and the qPCR instrument 900 in FIG. 5A. FIG. 6 is a schematic diagram of a light reflecting member 450 in FIG. 5A. As shown in FIGS. 5A to 6, one difference between this embodiment and the embodiment shown in FIG. 3A is that the optical calibration tool 400 of this embodiment replaces the light reflecting member 250 and the actuating member 280 shown in FIG. 3A with the different light reflecting member 450.

Specifically, as shown in FIG. 6, the light reflecting member 450 includes a prism 451 and a light splitting layer 452. The bottom of the prism 451 has two surfaces connected to each other. The surfaces are arranged between the light transmitting portions 243a, 243b. The light splitting layer 452 covers the surfaces. In some embodiments, the light splitting layer 452 is a semi-transmissive and semi-reflective film layer. As shown in FIG. 5A, when the third engaging port 141 is engaged with the first engaging port 111, the light emitted by the light emitter 120 of the optical calibration tool 400 can first enter the prism 451, be partially reflected by the left half of the light splitting layer 452, and then be partially transmitted through the right half of the light splitting layer 452 to reach the light receiver 930 of the qPCR instrument 900. As shown in FIG. 5B, when the third engaging port 141 is engaged with the second engaging port 112, the light emitted by the light emitter 920 of the qPCR instrument 900 can first be partially transmitted through the left half of the light splitting layer 452 enter the prism 451, be partially reflected by the right half of the light splitting layer 452, and then transmit through the prism 451 to reach the light receiver 130 of the optical calibration tool 400. Hence, the user can inspect the light emitter 920 and the light receiver 930 of the qPCR instrument 900 without plugging or rotating the second body 240 relative to the inspection slot 910, so that the calibration process can be performed quickly.

According to the foregoing recitations of the embodiments of the disclosure, it can be seen that in the optical calibration tool of the present disclosure, by engaging the third engaging port of the second body to the first engaging port of the first body, the light emitter in the optical calibration tool can be used to calibrate the light receiver in the qPCR instrument. Relatively, by engaging the third engaging port of the second body to the second engaging port of the first body, the light receiver in the optical calibration tool can be used to calibrate the light emitter in the qPCR instrument. That is, the optical calibration tool of the present disclosure can form different functional modules by different combinations of the first body and the second body. Furthermore, a user only needs to insert the second body into the inspection slot of the qPCR instrument to optically couple the light emitter of the optical calibration tool to the light receiver in the qPCR instrument, or to optically couple the light receiver of the optical calibration tool to the light emitter in the qPCR instrument. As such, the optical calibration tool of the present disclosure is easy for the user to operate, so that the calibration procedure can be performed quickly.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An optical calibration tool applied to a real-time quantitative polymerase chain reaction (qPCR) instrument, the qPCR instrument comprising an inspection slot, the inspection slot having a light incident region and a light exit region, the optical calibration tool comprising:
    a first body having a first engaging port and a second engaging port;
    a light emitter disposed in the first body;
    a light receiver disposed in the first body;
    a second body having a third engaging port and a channel communicated with each other, wherein the third engaging port is configured to selectively engage one of the first engaging port and the second engaging port; and
    a light reflecting member disposed in the channel and configured to be selectively optically coupled to one of the light incident region and the light exit region as the second body rotates relative to the inspection slot.

2. The optical calibration tool of claim 1, wherein the second body has a light transmitting portion adjoining the channel, when the third engaging port is engaged with the first engaging port, the light emitter is optically coupled to the light transmitting portion via the light reflecting member, and when the third engaging port is engaged with the second engaging port, the light receiver is optically coupled to the light transmitting portion via the light reflecting member.

3. The optical calibration tool of claim 2, wherein when the third engaging port is engaged with the first engaging port and the light transmitting portion is aligned with the light exit region, the light emitter is optically coupled to the light exit region sequentially via the light reflecting member and the light transmitting portion, and when the third engaging port is engaged with the second engaging port and the light transmitting portion is aligned with the light incident region, the light receiver is optically coupled to the light incident region sequentially via the light reflecting member and the light transmitting portion.

4. The optical calibration tool of claim 2, wherein the light transmitting portion is a hole.

5. The optical calibration tool of claim 2, wherein the light transmitting portion comprises a transparent material.

6. The optical calibration tool of claim 1, further comprising a neutral density filter disposed in the first body and adjoining the second engaging port.

7. The optical calibration tool of claim 1, further comprising a lens group disposed in the channel and adjoining the third engaging port.

8. The optical calibration tool of claim 1, wherein the third engaging port is configured to physically engage one of the first engaging port and the second engaging port.

9. The optical calibration tool of claim 8, wherein when the third engaging port is engaged with the first engaging port, the first engaging port is sleeved on an outer edge of the third engaging port.

10. The optical calibration tool of claim 8, wherein when the third engaging port is engaged with the second engaging port, the second engaging port is sleeved on an outer edge of the third engaging port.

* * * * *